(12) United States Patent
Havelund et al.

(10) Patent No.: US 6,489,292 B1
(45) Date of Patent: Dec. 3, 2002

(54) STABLE AQUEOUS INSULIN PREPARATIONS WITHOUT PHENOL AND CRESOL

(75) Inventors: Svend Havelund, Bagsværd; Niels C. Kaarsholm, Vanløse, both of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/441,702

(22) Filed: Nov. 16, 1999

Related U.S. Application Data
(60) Provisional application No. 60/110,707, filed on Dec. 3, 1998.

(30) Foreign Application Priority Data

Nov. 18, 1998 (DK) .......................................... 1998 01506

(51) Int. Cl.⁷ .............................................. A61K 38/28
(52) U.S. Cl. ................................ 514/3; 514/4; 530/303; 530/304
(58) Field of Search ........................ 514/3, 4; 530/303, 530/304

(56) References Cited

U.S. PATENT DOCUMENTS
5,474,978 A  12/1995  Bakaysa et al. ................ 514/4

FOREIGN PATENT DOCUMENTS
| EP | 0179442 A2 | 4/1986 |
| WO | WO 97/48414 | 12/1997 |

OTHER PUBLICATIONS
Whittingham et al., Biochemistry, vol. 37, pp. 11516–11523 (1998).
Whittingham et al., Biochemistry, vol. 36, pp. 2826–2831 (1997).

*Primary Examiner*—Christopher S. F. Low
*Assistant Examiner*—Abdel A. Mohamed
(74) *Attorney, Agent, or Firm*—Reza Green, Esq.

(57) ABSTRACT

Stable, aqueous insulin formulations without phenol and m-cresol which are suitable for pulmonary delivery and for delivery when phenol and m-cresol are undesirable are disclosed. The formulations provide increased convenience for the patient.

21 Claims, No Drawings

STABLE AQUEOUS INSULIN PREPARATIONS WITHOUT PHENOL AND CRESOL

CROSS-REFERENCE TO RELATED APPLICATIONS

This application claims priority under 35 U.S.C. 119 of Danish application PA No. 1998 01506 filed Nov. 18, 1998, and also claims the benefit of U.S. Provisional application No. 60/110,707 filed Dec. 3, 1998, the contents of which are fully incorporated herein by reference.

FIELD OF THE INVENTION

The present invention relates to stable, aqueous insulin formulations without phenol and m-cresol suitable for pulmonary delivery and for delivery when phenol and m-cresol are undesirable, providing increased convenience for the patient.

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is more or less completely lost. About 2% of all people suffer from diabetes.

Since the introduction of insulin in the 1920's, continuous strides have been made to improve the treatment of diabetes mellitus. To help avoid extreme glycaemia levels, diabetic patients often practice multiple injection therapy, whereby insulin is administered with each meal.

In solution, the self-association pattern of insulin is a complex function of protein concentration, metal ions, pH, ionic strength and solvent composition. For the currently used soluble preparations containing U100 insulin, zinc ions, isotonic agent and phenolic preservative, the following equilibria must be considered:

$$6In \rightleftharpoons 3In_2$$

$$3In_2 + 2Zn^{2+} \rightleftharpoons In_6(T_6)$$

$$T_6 \rightleftharpoons T_3R_3 \rightleftharpoons R_6$$

The known degradation patterns of insulin include a) fibril formation; b) deamidations at A18, A21 and B3; c) dimerisations via transamidation or Schiff-base formation; d) disulfide exchange reactions.

According to Brange (Stability of Insulin, Kluwer Academic Press,1994), each of these degradation reactions proceed much faster in the monomeric state than in the hexameric state. Therefore, the most efficient means of stabilising insulin preparations is by pushing the above equilibrium as far to the right as possible. In addition to this general effect of mass action, the reactivity of selected residues is further modified depending on their direct involvement in the T→R conformational change. Thus, the reactivity of B3Asn is much lower in the R-state (when the residue resides in an α-helix) than in the T-state.

The interconversion between $T_6$, $T_3R_3$ and $R_6$ conformations of the two zinc insulin hexamer is modulated by ligand binding to the $T_3R_3$ and $R_6$ forms. Anions such as chloride have affinity for the fourth coordination position in the metal ions of $T_3R_3$ and $R_6$, while preservatives such as phenol binds to hydrophobic pockets located near the surfaces of the $T_3R_3$ and $R_6$ forms (Derewenda, Nature 338, 594, 1989 and, Brzovic, Biochemistry 33, 130557, 1994). By the use of $Co^{2+}$ insulin it has been shown that the combined effect of anion and phenol binding is particularly efficient in stabilising the $R_6$ state. (Brader, Trends Biochem. Sci. 30, 6636, 1991 and; Bloom, J. Mol. Biol. 245, 324, 1995). Furthermore, for both $Zn^{2+}$- and $Co^{2+}$ insulin it has been shown that phenol is much more efficient than m-cresol in inducing R-state in the insulin hexamer (Wollmer, Biol. Chem. Hoppe-Seyler 368, 903, 1987 and, Choi, Biochemistry 32, 11638, 1993). High affinity phenol derivatives inducing R-state are 7-hydroxy-indol ((Dodson, Phil. Trans. R. Soc. Lond. A 345, 153, 1993) resorcinol and 2,6- and 2,7-dihydroxy-naphtalen ((Bloom, J. Mol. Biol. 245, 324, 1995).

The physical denaturation of insulin is known as fibrillation. In the fibrillar state extended peptide chains are laying parallel or anti parallel and hydrogen bonded to each other, so-called β-structure or β-pleated sheets. Fibrils represent usually the lowest state of energy of the protein, and only harsh conditions such as strong base may enable a regeneration from this state to the native state of correctly folded protein. Factors that promote the rate of formation of fibrils are increasing the temperature, increasing the surface area between the liquid and the air phase and, for zinc-free insulin, increasing the concentration. For hexameric zinc-insulin the rate of fibril formation decreases with increasing concentration. The formation of fibrils is believed to proceed via monomerization of insulin. Fibrils of insulin have the appearance of gels or precipitates.

Insulin derivatives having truncations in the C-terminal of the B-chain, e.g. des-pentapeptide (B26–B30) insulin and des-octapeptide (B23–B30) insulin are more prone to form fibrils than human insulin. Insulin analogues which dissociate readily from the hexameric unit to the monomeric form, e.g. the AspB28 human insulin and the LysB28-ProB29 human insulin, are likewise more prone to form fibrils than human insulin.

The native state of insulin is stabilised by bringing about the conditions that stabilises the hexameric unit, i.e. the presence of zinc ions (2–4 zinc/hexamer), phenol (0.1–0.5% w/v) and sodium chloride (5–150 mM).

Addition of agents that reduce the surface tension at the air-liquid interface further reduces the propensity to fibril formation. Thus, polyethylene glycol, polypropylene glycol and co-polymers hereof with an average molecular weights of about 1800 have found use as stabilisers in concentrated insulin solutions for infusion pumps (Grau, 1982. In: Neue Insuline (Eds. Petersen, Schlüter & Kerp), Freiburger Graphische Betriebe, pp. 411–419 and Thurow,1981: patent No. DE2952119A1). For a comprehensive review on the physical stability of insulin see Brange 1994, Stability of Insulin, Kluwer Academic Publisher, pp. 18–23.

Most of the chemical degradation of insulin in preparations is due to reactions involving the carboxamide function of the asparagine residues, in particular residues B3 and A21. Hydrolysis of the amide groups leads to desamido derivatives, and transamidation involving an amino group from another molecule leads to covalently linked dimers and, after similar consecutive reactions, to trimers and higher polymers.

In acid solution AsnA21 is the most reactive, leading to AspA21 insulin (Sundby, J. Biol. Chem. 237, 3406, 1962). In crude insulin of bovine and porcine origin, obtained by acid ethanol extraction, the most abundant dimers isolated were AspA21-GlyA1 and AspA21-PheB1 linked (Helbig 1976, Insulindimere aus der B-Komponente von Insulinpräparationen, Thesis at the Rheinisch-Westfälischen Technischen Hochschule, Aachen).

In neutral solution, which is the preferred embodiment of insulin preparations for injection therapy, AsnB3 is the most susceptible residue. Degradation products include AspB3 insulin, AspB3-GlnB4 isopeptide insulin, and dimers and higher polymers where AspB3 provides the carbonyl moiety of a peptide bond with an amino group of another molecule. For a comprehensive review on the chemical stability of insulin see Brange 1994, Stability of Insulin, Kluwer Academic Publisher, pp. 23–36. As for the physical stability conditions that stabilises the hexameric unit, i.e. the presence of zinc ions (2–4 zinc/hexamer), phenol (0.1–0.5% w/v) and sodium chloride (5–150 mM), decrease the rate of formation of degradation products during storage at neutral pH.

A different type of polymerisation reaction is observed when the conditions that stabilises the hexameric unit is neglected. Thus, in the absence of zinc, phenol and sodium chloride, and using a temperature of 50° C., disulfide-linked dimers and high molecular weight polymers are the prevailing products formed. The mechanism of formation is a disulfide interchange reaction, resulting from β-elimination of the disulfides (Brems, Protein Engineering 5, 519, 1992).

Solubility of insulin is a function of pH, metal ion concentration, ion strength, phenolic substances, solvent composition (polyols, ethanol and other solvents), purity, and species (bovine, porcine, human, other analogues). For a review see Brange: Galenics of Insulin, Springer-Verlag 1987, p.18 and 46.

The solubility of insulin is low at pH values near its isoelectric pH, i.e. in the pH range 4.0–7.0. Highly concentrated solutions of porcine insulin (5000 U/ml~30 mM) have been brought about at acid pH (Galloway, Diabetes Care 4, 366, 1981), but the insulin in the formulation is highly instable due to deamidation at AsnA21. At neutral pH highly concentrated solutions of zinc free insulin can be made, but these are unstable due to a high rate of polymerisation and deamidation at AsnB3. Porcine zinc insulin solutions at neutral pH comprising phenol have been reported physical stable at concentrations of 1000 U/ml at elevated temperature, but become supersaturated when the temperature is lowered to 4° C. (Brange and Havelund in Artificial Systems for Insulin Delivery, Brunetti et al. eds, Raven Press 1983).

In order to reduce the inconvenience of insulin injections much attention has been given to alternative routes of administration (for an overview see Brange and Langkjaer in Protein Delivery: Physical Systems, Sanders and Hendren, eds., Plenum Press 1997). Pulmonary delivery seems to be the most promising of these (Service, Science 277, 1199, 1997). Insulin can be given aerolised in the form of dry powder or as nebulised droplets from an insulin solution. The efficacy might be enhanced by coached breathing (Gonda, U.S. Pat. No. 5,743,250) and addition of an absorption enhancer (Baekstroem, U.S. Pat. No. 5,747,445) or protease inhibitors (Okumura, Int. J. Pharm. 88, 63, 1992).

The bioavailability of a nebulised concentrated insulin solution (500 U/ml) was shown to be 20–25% as compared to a subcutaneous injection (Elliot, Aust. Paediatr. J. 23, 293, 1987). By using 30–50 μl insulin solution per puff the insulin solution need to be 5–20 times more concentrated than the usual concentration of 0.6 mM. By using a single dose container, e.g. a blister pack (Gonda, U.S. Pat. No. 5,743, 250), the demand for a preservative is abolished. Most insulin formulations are preserved by the toxic, mucose irritating and unpleasant odorous phenol and m-cresol. However, omitting phenols will cause stability problems. In addition to the bacteriostatic efficacy, the phenols act as physico-chemical stabilisers of insulin in combination with zinc ions. So, it is preferred that formulations of insulin for inhalation are made with a minimum concentration of phenol or that phenol has been replaced by more acceptable substitutes.

DESCRIPTION OF THE INVENTION

Definitions

By "analogue of human insulin" (and similar expressions) as used herein is meant human insulin in which one or more amino acids have been deleted and/or replaced by other amino acids, including non-codeable amino acids, or human insulin comprising additional amino acids, i.e. more than 51 amino acids.

By "derivative of human insulin" (and similar expressions) as used herein is meant human insulin or an analogue thereof in which at least one organic substituent is bound to one or more of the amino acids.

By "non-phenolic substance" is meant an organic compounds which does not contain a structural fragment consisting of a benzene ring to which a hydroxy group is bound.

By "stabiliser" is meant a substance which acts like phenol and m-cresol by inducing the $R_6$ conformation of the two zinc insulin hexamer.

By "phenol mimic" is meant a non-phenolic substance which is capable of inducing the $R_6$ conformation of the two zinc insulin hexamer.

BRIEF DESCRIPTION OF THE INVENTION

It is an object of the present invention to provide a stable insulin formulation which is useable for pulmonary delivery, and which has an increased convenience for the patient without deteriorating the physical and chemical stability.

Furthermore, it is an object of the invention to provide a stable insulin formulation for delivery, when the presence of phenol and m-cresol are undesirable, in single dose containers without a preservative or in multiple dose containers with other preservatives.

These objects have unexpectedly been accomplished by providing an insulin formulation in which phenol and m-cresol, commonly used in insulin formulations, have been replaced with a non-phenolic substance which acts like phenol and m-cresol by inducing the $R_6$ conformation of the two zinc insulin hexamer. These compounds are subsequently named stabilisers.

Unexpectedly, such stabilisers have been found among the non-toxic and pleasant odorous or non-odorous substances selected from the group of monoterpenes, especially bicyclic monoterpenols as borneol and isopinocampheol, tricyclic aliphatic alcohols as 1-adamantanol and purines as purin and adenine.

Accordingly, the present invention relates to an aqueous insulin formulation comprising: human insulin or an analogue or a derivative thereof, zinc ions and a non-phenolic stabiliser which is capable of inducing the $R_6$ conformation of the two zinc insulin hexamer.

Furthermore, the stabilisers provided by the present invention may be used in insulin solutions for pump treatment or for injection without addition of a preservative or in combination with other preservatives than phenol and m-cresol.

Preferred Embodiments

The non-phenolic stabiliser is preferably selected from the group consisting of bi- or tricyclic aliphatic alcohols and purines.

In a preferred embodiment the non-phenolic stabiliser is a bicyclic aliphatic alcohol, preferably a monoterpenol, more preferably isopinocampheol, 2,3-pinandiol, myrtanol, borneol, norborneol or fenchol.

In another preferred embodiment the non-phenolic stabiliser is a tricyclic aliphatic alcohol, preferably 1-adamantanol.

In another preferred embodiment the non-phenolic stabiliser is a purine, preferably purine, adenine, guanine or hypoxanthine.

All of the above mentioned non-phenolic stabiliser have been found to be non-toxic and pleasant odorous or non odorous.

The insulin formulation preferably comprises at least 3 molecules of said non-phenolic stabiliser per six molecules of insulin, preferably up to 50 mM of said non-phenolic substance.

The insulin formulation preferably contains 0.3 to 20 mM, preferably 0.6 to 15 mM, more preferably 3 to 15 mM of human insulin or an analogue or a derivative thereof.

The stability of the insulin formulation is further improved when the concentration of chloride is kept below 50 mM, preferably below 30 mM, and more preferably in the range of 5 to 20 mM.

A remarkable stability of the insulin formulation is obtained when it comprises less than 10 mM of any anions other than chloride and acetate.

In a particular embodiment the insulin may comprise a low amount of phosphate buffer, preferably up to 5 mM of phosphate.

Insulin formulations of the invention comprising 2.0 to 4.5 $Zn^{2+}$ ions, preferably 2.5 to 3.5 $Zn^{2+}$ ions per six molecules of insulin, are very stable.

In an alternative embodiment, the insulin formulation of the invention comprises 2.5 to 4.5 $Zn^{2+}$ ions, preferably 3 to 4 $Zn^{2+}$ ions per six molecules of insulin.

Surprisingly, it is possible to add a relatively high concentrations of zwitterions such as glycylglycine and glycine to the insulin formulation of the invention without decreasing the solubility of insulin. Glycylglycine act as buffer at neutral pH and furthermore increase the dissolution rate of zinc insulin at neutral to basic pH due to a moderately zinc chelating effect. Also, glycylglycine may act as a scavenger for amine reactions during the storage time. Thus, in a preferred embodiment the insulin formulation of the invention further comprises 5 to 150 mM of a zwitterionic amine, preferably glycylglycine or glycine.

In another preferred embodiment the insulin formulation comprises a zwitterionic amine selected from the group consisting of BICINE, TRICINE and BIS-TRIS.

In another preferred embodiment the insulin formulation comprises a zwitterionic amine selected from Good's buffers.

In a preferred embodiment the insulin formulation of the invention further comprises 5 to 50 mM of trishydroxymethylaminomethan, which acts as a buffer at neutral pH and as a scavenger for amine reactive compounds.

In another preferred embodiment the insulin formulation of the invention comprises between 0.001% by weight and 1% by weight of a non-ionic surfactant, preferably Tween 20 or Poloxamer 188. A nonionic detergent can be added to stabilise insulin against fibrillation during storage and nebulisation.

In a preferred embodiment the insulin used is human insulin.

In another preferred embodiment the insulin used is an analogue of human insulin wherein position B28 is Asp, Lys, Leu, Val or Ala and position B29 is Lys or Pro; or des (B28–B30), des(B27) or des(B30) human insulin.

The preferred analogues of human insulin are those in which position B28 is Asp or Lys, and position B29 is Lys or Pro, preferably $Asp^{B28}$ human insulin or $Lys^{B28}Pro^{B29}$ human insulin.

The insulin analogue can also be selected among those disclosed generically as well as specifically in EP 885 961 (such as (B3)Lys, (B28)lle, (A21)Gly human insulin).

In another preferred embodiment the insulin is selected from the group of soluble long-acting insulin derivatives such as derivatives of human insulin having one or more lipophilic substituents, preferably acylated insulins.

The insulin derivative according to this embodiment is preferably selected from the group consisting of B29-$N^\epsilon$-myristoyl-des(B30) human insulin, B29-$N^\epsilon$-palmitoyl-des(B30) human insulin, B29-$N^\epsilon$-myristoyl human insulin, B29-$N^\epsilon$-palmitoyl human insulin, B28-$N^\epsilon$-myristoyl $Lys^{B28}$ $Pro^{B29}$ human insulin, B28-$N^\epsilon$-palmitoyl $Lys^{B28}$ $Pro^{B29}$ human insulin, B30-$N^\epsilon$-myristoyl -$Thr^{B29}Lys^{B30}$ human insulin, B30-$N^\epsilon$-palmitoyl-$Thr^{B29}Lys^{B30}$ human insulin, B29-$N^\epsilon$-(N-palmitoyl -γ-glutamyl)-des(B30) human insulin, B29-$N^\epsilon$-(N-lithocholyl-γ-glutamyl)-des(B30) human insulin, B29-$N^\epsilon$-(ω-carboxyheptadecanoyl)-des(B30) human insulin and B29-$N^\epsilon$-(ω-carboxyheptadecanoyl) human insulin.

The most preferred insulin derivative is B29-$N^\epsilon$-myristoyl-des(B30) human insulin or B29-$N^\epsilon$-(N-lithocholyl-γ-glutamyl)-des(B30) human insulin.

The above mentioned soluble long acting insulin derivatives bind albumin and have been designed to provide a constant basal supply of insulin (Markussen, Diabetologia 39, 281, 1996). Subcutaneous administration once or twice daily secure the required basal delivery of insulin, whereas several daily inhalations are recommended using pulmonary administration, preferably in connection with meals.

The insulin derivatives have a protracted onset of action and may thus compensate the very rapid increase in plasma insulin normally associated with pulmonary administration. By careful selection of the type of insulin, the present invention enables adjustment of the timing, and in order to obtain the desired insulin profile.

In a particular embodiment of the present invention, the insulin formulation comprises an insulin analogue or human insulin as well as an insulin derivative.

The insulin preparation of the present invention preferably has a pH value in the range of 7 to 8.5, more preferably 7.4 to 7.9.

The present invention also relates to a method of treating type I or type II diabetes, comprising administering (preferably by pulmonary delivery) to a patient in need of such treatment an insulin formulation according to any of the preceding claims.

In a preferred embodiment, insulin formulation is administered in connection with meals.

This invention is further illustrated by the following examples which, however, are not to be construed as limiting.

EXAMPLE 1

27.5 ml of a 21 mM insulin stock solution was made by dissolving 3.707 g zinc free human insulin in 14 ml water and adding 2888 µl of 0.1 M $ZnCl_2$ and 7 ml water before adjusting pH to 7.5 by 0.2 M NaOH and finally adding water to 27.5 ml, calculating the specific volume of insulin as 0.7 µl/mg. The stock solution was filtrated. A preparation of 3.5 ml 15 mM insulin was then made by adding 23 µl 2.3 M stabiliser in ethanol, 49 µl 0.5 M glycylglycine and 35 µl 1% Tween 20 and water to 3.5 ml. The solution was thereafter diluted with medium containing sodium chloride 15 mM, glycylglycine 7 mM, Tween 20 0.01%, pH 7.5 to 12, 9, 6, 3 and 0.6 mM insulin and stored at 5° C. for visual inspection. The reference solution was made by the same way but without adding a stabiliser. The chemical stability of the insulin solutions were followed at 37° C. for two concentrations, 3 and 15 mM, by determination of covalent insulin polymer by size exclusion chromatography. The analysis of insulin polymer was performed on Waters PROTEIN PAK 125 (250×8 mm) with an eluent containing 2.5 M acetic acid, 4 mM L-arginine and 20%(V/V) acetonitrile at a flow rate of 1 ml/min. and ambient temperature. Detection was performed with a tunable absorbance detector (Waters 486) at 276 nm. Injection volume were 8 and 3 ml for 3 and 15 mM insulin solutions, respectively. The results are shown in Table 1.

EXAMPLE 2

3.26 g human insulin (0.4 equivalent $Zn^{2+}$ per insulin) was dispersed in water in 18 ml water on icebath and added 490 µl 0.5 M glycylglycine and 1628 µl sodium hydroxide (3.1 equivalent) and stirred slowly overnight at 5° C. 613 µl 0.1 M zinc chloride (0.1 equivalent of zinc) was then added the solution, pH adjusted to 7.5 by 410 µl 1 M hydrochloric acid (0.8 equivalent of chloride) and the volume adjusted to 25 ml by water. Finally the stock solution of 21 mM insulin was filtrated. 3.57 ml of the stock solution was added 50 µl 1% tween 20, 750 µl 0.1 M stabiliser and 630 µl water to obtain 5 ml 15 mM insulin formulation. Finally the preparation was diluted with medium containing sodium chloride, glycylglycine and detergent to obtain 12, 9, 6, and 3 mM of human insulin and stored at 5° C. for visual inspection. The chemical stability of 3 and 15 mM insulin solutions were followed at 37° C. by determination of covalent insulin polymer by size exclusion chromatography. The results are presented in Table 2.

Determination of $R_6$ Conformation

The inducement of $R_6$ state by a given ligand is measured by the concentration dependence of the appearance of 1H-NMR resonances in the 5.0–6.5 ppm region in a ligand titration of zinc-insulin hexamers as described by Brzovic, P. S., Choi, W. E., Borchardt, D., Kaarsholm, N. C. & Dunn, M. F. (1994) Biochemistry 33, 13057–13069.

Alternatively, the relative efficacy by which a given ligand induces $R_6$ state may be estimated by spectophometric titration using the indicator 4-hydroxy, 3-nitro- benzoic acid as described by Huang, S. T., Choi, W. E., Bloom, C., Leuenberger, M. & Dunn, M. F. (1997) Biochemistry 36, 9878–9888. The endpoint of the spectrophotometric titration shall show at least 50% of the absorbance obtained as endpoint by titration with phenol e.g. at conditions of 3 mM insulin, 1 mM zinc acetate, 10 mM sodium chloride, 0.2 mM 4-hydroxy-3-nitro-benzoic acid, 50 mM tris-perchlorate pH 8.0 at 23 C or e.g. an comparison at conditions of 9 mM insulin, 4.5 mM zinc as chloride, 15 mM total chloride, 0.15 mM 4-hydroxy-3-nitro-benzoic acid, 7 mM diglycine, pH 7.5 at 23 C, measured at 443 nm.

TABLE 1

Stability of human insulin at equimolar concentrations of non phenolic stabilisers according to example 1 (0.5 $Zn^{2+}$/insulin, NaCl 15 mM, glycylglycine 7 mM, tween 20 0.01% and pH 7.5).

| Stabilisers equimolar to insulin (ex. 1): | Physical stability of solution at 4 weeks and 5° C. Maximal insulin concentration at which the solution was without precipitation up to 15 mM (3, 6, 9, 12, 15 mM) | Chemical stability at 37° C. (% polymer/week) Insulin solution of 3 mM and 15 mM | |
|---|---|---|---|
| (−)-isopinocampheol | 15 | 0.53 | 0.56 |
| (+)-isopinocampheol | 12 | 0.49 | 0.61 |
| (−)-borneol | 9 | 0.43 | 0.47 |
| (+)-borneol | 9 | 0.47 | 0.61 |
| (+)-fenchol | 15 | 0.50 | 0.97 |
| (−)-trans-myrtanol | 15 | 0.64 | 0.95 |
| phenol | 15 | 0.37 | 0.39 |
| reference | 6 | 0.94 | 1.49 |

TABLE 2

Stability of human insulin at equimolar concentrations of non phenolic stabilisers according to example 2 (0.5 $Zn^{2+}$/insulin, NaCl 15 mM, glycylglycine 7 mM, tween 20 0.01%, pH 7.5).

| Stabilisers equimolar to insulin (ex. 2): | Physical stability of solution at 4 weeks and 5° C. Maximal insulin concentration at which the solution was without precipitation up to 15 mM (3, 6, 9, 12, 15 mM) | Chemical stability at 37° C. (% polymer/week) Insulin solution of 3 mM and 15 mM | |
|---|---|---|---|
| purine | 15 | 0.58 | 0.71 |
| adenine | 9 | 0.59 | 0.77 |
| phenol | 15 | 0.32 | 0.29 |
| reference | 15 | 0.71 | 1.03 |

We claim:

1. An aqueous insulin formulation comprising: human insulin or an analogue or a derivative thereof for therapeutic administration, zinc ions and a non-phenolic stabiliser, wherein said zinc ions and non-phenolic stabilizer induce the $R_6$ conformation of the two zinc insulin hexamer.

2. An insulin formulation according to claim 1 comprising at least 3 molecules of said non-phenolic substance per six molecules of insulin.

3. An insulin formulation according to claim 1 comprising 0.3 to 20 mM of human insulin or an analogue or a derivative thereof.

4. An insulin formulation according to claim 1 comprising less than 50 mM chloride.

5. An insulin formulation according to claim 1 comprising less than 10 mM of any anions other than chloride and acetate.

6. An insulin formulation according to claim 1 comprising up to 5 mM of phosphate.

7. An insulin formulation according to claim 1 comprising 2.0 to 4.5 $Zn^{2+}$ ions per six molecules of insulin.

8. An insulin formulation according to claim 1 further comprising 5 to 50 mM of trishydroxymethylaminomethan.

9. An insulin formulation according to claim 1, further comprising between 0.001% by weight and 1% by weight of a surfactant.

10. An insulin formulation according to claim 1 comprising human insulin.

11. An insulin preparation according to claim 1, comprising an insulin analogue or human insulin as well as an insulin derivative.

12. An aqueous insulin formulation according to claim 1, wherein said non-phenolic substance is selected from the group consisting of bi- or tricyclic aliphatic alcohols and purines.

13. An insulin preparation according to claim 1, comprising an analogue of human insulin wherein position B28 is Asp, Lys, Leu, Val or Ala and position B29 is Lys or Pro; or des(B28–B30), des(B27) or des(B30) human insulin.

14. An insulin preparation according to claim 13, comprising an analogue of human insulin wherein position B28 is Asp or Lys, and position B29 is Lys or Pro.

15. An insulin formulation according to claim 1, further comprising 3 to 150 mM of a zwitterionic amine.

16. An insulin formulation according to claim 15 wherein said zwitterionic amine is glycylglycine or glycine.

17. An insulin formulation according to claim 15 wherein said zwitterionic amine is N,N-bis[2-Hydroxyethyl]glycine (BICINE), N-tris [Hydroxymethyl]methylglycine (TRICINE), or bis[2-Hydroxyethyl]iminotris [hydroxymethyl]methane (BIS-TRIS).

18. An insulin formulation according to claim 15 wherein said zwitterionic amine is a buffer selected from Good's buffers.

19. An insulin preparation according to claim 1, comprising a derivative of human insulin having one or more lipophilic substituents.

20. An insulin preparation according to claim 19, wherein the insulin derivative is selected from the group consisting of B29-$N^\epsilon$-myristoyl-des(B30) human insulin, B29-$N^\epsilon$-palmitoyl-des(B30) human insulin, B29-$N^\epsilon$-myristoyl human insulin, B29-$N^\epsilon$-palmitoyl human insulin, B28-$N^\epsilon$-myristoyl Lys$^{B28}$Pro$^{B29}$ human insulin, B28-$N^\epsilon$-palmitoyl Lys$^{B28}$Pro$^{B29}$ human insulin, B30-$N^\epsilon$-myristoyl-Thr$^{B29}$Lys$^{B30}$ human insulin, B30-$N^\epsilon$-palmitoyl-Thr$^{B29}$Lys$^{B30}$ human insulin, B29-$N^\epsilon$-(N-palmitoyl-$\gamma$-glutamyl)-des(B30) human insulin, B29-$N^\epsilon$-(N-lithocholyl-$\gamma$-glutamyl)-des(B30) human insulin, B29-$N^\epsilon$-($\omega$-carboxyheptadecanoyl)-des(B30) human insulin and B29-$N^\epsilon$-($\omega$-carboxyheptadecanoyl) human insulin.

21. An insulin preparation according to claim 20 wherein the insulin derivative is B29-$N^\epsilon$-myristoyl-des(B30) human insulin or B29-$N^\epsilon$-(N-lithocholyl-$\gamma$-glutamyl)-des(B30) human insulin.

* * * * *